United States Patent [19]
Shofner et al.

[11] Patent Number: 5,929,460
[45] Date of Patent: Jul. 27, 1999

[54] HIGH THROUGHPUT NEP MEASUREMENT

[75] Inventors: Frederick M. Shofner; David A. Hinkle, both of Knoxville, Tenn.

[73] Assignee: Premier Polytronics Limited, Coimbatore, India

[21] Appl. No.: 08/944,912

[22] Filed: Oct. 6, 1997

[51] Int. Cl.[6] .................................................. G01N 21/00
[52] U.S. Cl. ................ 250/574; 250/559.01; 356/238.3; 73/160
[58] Field of Search ............................... 250/221, 222.1, 250/559.01, 574; 73/160; 356/238.3, 383–386; 19/23

[56] References Cited

U.S. PATENT DOCUMENTS

| | | |
|---|---|---|
| 5,270,787 | 12/1993 | Shofner et al. . |
| 5,321,496 | 6/1994 | Shofner et al. ...................... 356/238.3 |
| 5,394,480 | 2/1995 | Shofner et al. ..................... 250/559.01 |
| 5,410,401 | 4/1995 | Shofner et al. . |
| 5,430,301 | 7/1995 | Shofner et al. . |
| 5,469,253 | 11/1995 | Shofner et al. . |
| 5,539,515 | 7/1996 | Shofner et al. . |

*Primary Examiner*—Stephone Allen
*Attorney, Agent, or Firm*—Carter & Schnedler, P.A.

[57] ABSTRACT

Apparatus and methods for measuring the quantity and size distribution of nep-like entities in a fiber sample. An individualizer presents entities, such as fibers and neps, to a laterally elongated acceleration/deceleration gas flow nozzle having a laterally-extending sensing volume defined within the nozzle perpendicular to gas flow through the nozzle. The feed rate is such that multiple individualized entities are simultaneously presented to the sensing volume. A sensor output device produces a signal indicating the total amount of material within the sensing volume at any given point in time, such that the sensor output signal has a background resulting from fibers, and occasional signal pulses representing neps. An analyzer samples the signal at a sampling rate at least approximating the transit time of a nep-like entity through the sensing volume, and employs pre-sample and post-sample averaging background suppression to recognize a signal amplitude indicative of a nep-like entity.

9 Claims, 6 Drawing Sheets

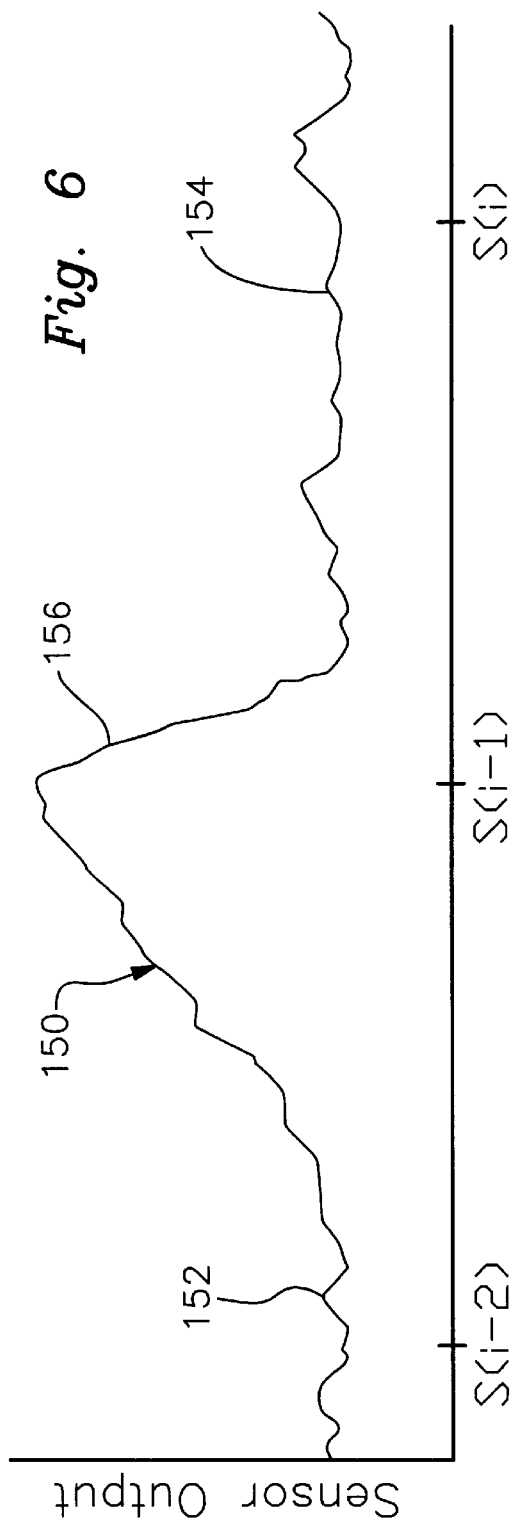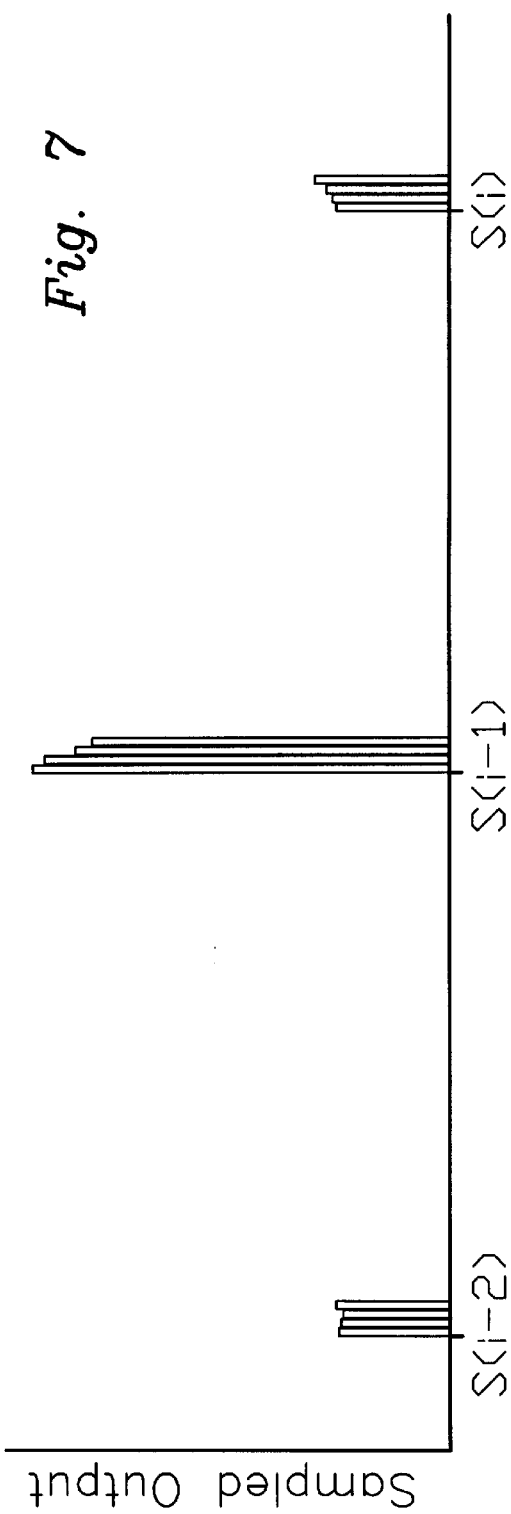

ial entities in a fiber sample and,
more particularly, to measuring the quantity and size distribution of nep-like entities in a fiber sample.

HIGH THROUGHPUT NEP MEASUREMENT

BACKGROUND OF THE INVENTION

This invention relates generally to measurement and classification of individual entities in a fiber sample and, more particularly, to measuring the quantity and size distribution of nep-like entities in a fiber sample.

Testing of fiber samples, such as, but not limited to, cotton, is important for determining the market value of a particular batch of material, as well as for determining a suitable usage and what processing may be required in gins or spinning mills. Today, nearly 100% of the cotton grown in the United States is classed employing testing instruments. Testing in general includes determining such characteristics as fiber length, as well as the content of undesired textile entities such as trash and neps.

Apparatus for measuring characteristics of single entities in fiber samples is disclosed in Shofner et al U.S. Pat. Nos. 5,270,787, 5,410,401, 5,430,301, 5,469,253 and 5,539,515, the entire disclosures of which are hereby expressly incorporated by reference.

Prior art apparatus as disclosed in U.S. Pat. Nos. 5,270,787, 5,410,401, 5,430,301, 5,469,253 and 5,539,515 includes an individualizer which processes a fiber sample into individual entities, including fibers and nep-like entities (including actual neps), and delivers the entities one at a time to a fluid stream. (Trash may be separated and delivered to another fluid stream.) A nozzle orients the entities so that each entity along its length (major dimension) is generally parallel with the direction of fluid flow. The entities are directed through a sensing volume which utilizes electro optical sensors to generate characteristic signals corresponding to each entity passing through the sensor volume. Thus the sensing volume is defined by a beam of light. The signals are analyzed to count and determine various characteristics of the entities, such as their size.

Nozzle considerations are in particular discussed in Shofner et al U.S. Pat. No. 5,410,401. Such an acceleration/deceleration gas flow nozzle is circular in cross-section, and has an inlet section or bore which tapers down to a minimum diameter, for example 0.125 inch, at a throat or intermediate section, followed by an outlet section or bore which tapers out. Due to acceleration whereby the leading end of a fiber tends to travel faster than its trailing end, a well-designed nozzle is capable of straightening individual fibers for presentation to the sensing volume. An optical aperture at the throat or intermediate section at a right angle to the nozzles accommodates the light beam which defines the sensing volume.

As is in particular disclosed in U.S. Pat. Nos. 5,430,301, 5,469,253 and 5,539,515 different entity types, e.g. fiber, trash and neps, produce characteristic waveforms at the sensor output. Indeed, to some extent entities such as neps can be defined by the sensor output waveforms they produce. Thus, the apparatus of U.S. Pat. Nos. 5,430,301, 5,469,253 and 5,539,515 analyzes the waveforms to count and classify individual entities in the fiber sample passing through the sensing volume one at a time.

A limiting characteristic of the prior art apparatus as disclosed in Shofner et al U.S. Pat. Nos. 5,270,787, 5,410,401, 5,430,301, 5,469,253 and 5,539,515 is that individualized entities are presented for analysis one at a time to the light beam defining the sample volume. Further, samples do not enter the sample volume immediately one after the other (i.e. head-to-tail). Rather, there is a space between the individualized entities entering the sample volume such that typically the sample volume is occupied by an entity, or by a portion of an entity, only about one-fourth of the time.

Taking cotton as an example, in relative terms nearly all of a sample typically comprises fibers, although other entities are present. In a ten-gram cotton sample, there are typically approximately $2.5 \times 10^6$ fibers and $2.5 \times 10^3$ neps, as well as $2.5 \times 10^3$ trash particles. Therefore, there are typically approximately one thousand times more fibers than neps, although nep concentration may range from ten neps per gram of fiber sample to one thousand neps per gram of fiber sample.

These considerations, as well as others, severely limit the throughput, and accordingly the feasible sample size that can be processed in a reasonable amount of time. Thus, the apparatus of Shofner et al U.S. Pat. Nos. 5,270,787, 5,410,401, 5,430,301, 5,469,253 and 5,539,515 may take two hundred seconds to process a fiber sample weighing only 0.5 gram.

SUMMARY OF THE INVENTION

Accordingly, it is an object of the invention to provide fiber testing apparatus with a much higher throughput than is achieved by prior art measurement devices.

It is a related object of the invention to provide fiber sample testing apparatus which is capable of analyzing larger sample sizes (for statistically improved results) in less time.

As an example, and in contrast to the prior art, the measurement apparatus of the invention is capable of processing a fiber sample weighing ten grams in thirty seconds, resulting in a throughput approximately 140 times that of the prior art apparatus.

Very briefly, the measurement apparatus of the invention includes an acceleration/deceleration gas flow nozzle through which entities are carried within a gas flow. As is known, an acceleration/deceleration gas flow nozzle includes an inlet section tapering to a minimum cross-sectional area at a throat, and an output section expanding from the minimum cross-sectional area. However, unlike the nozzles of the above-identified U.S. patents, and in particular U.S. Pat. No. 5,410,401, which are circular in cross-section and by means of which entities are directed through a sensing volume one at a time, the acceleration/deceleration gas flow nozzle of the subject invention is laterally elongated (for example, with a lateral extent of eight inches and a throat spacing of one-eighth inch) to accommodate multiple fibers within the nozzle and, more particularly, within the sensing volume, at one time. By way of example, and not limitation, an average of thirty fibers, or portions thereof, may be in the sensing volume at one time.

The sensing volume is defined within the nozzle perpendicular to gas flow through the nozzle, one function of the nozzle being to straighten fiber for presentation to the sensing volume. The sensing volume may be defined by a light beam and an associated optical sensor.

The apparatus includes an individualizer for individualizing entities in the fiber sample, and introducing the entities into the gas flow stream directed into the nozzle at a rate such that multiple individualized entities are simultaneously presented to the sensing volume. A preferred individualizer is disclosed in concurrently-filed United States patent application Ser. No. 08/944,913, filed Oct. 6, 1997, by Frederick M. Shofner and Christopher K. Shofner, titled "Aeromechanical Individualizer," the entire disclosure of which is hereby expressly incorporated by reference.

Associated with the sensing volume is a sensor output device, such as a photo optical sensor, which produces a signal indicating the total amount of material within the sensing volume at any given point in time.

An analyzer is connected to the sensor output device for detecting and sizing nep-like entities.

A characteristic of the sensor output signal is that it has a relatively high and fluctuating background signal level caused by portions of multiple fibers within the sensing volume at one time, punctuated by somewhat higher amplitude pulses resulting from the presence of individual neps within the sensing volume. In relative terms compared to fiber, neps are rare, and normally occur one at a time.

Accordingly, the analyzer must be capable of detecting entity signals, in particular signals resulting from nep-like entities, in a large and fluctuating background of signals resulting from other entities, in particular fiber.

In one embodiment, the analyzer samples the signal from the sensor output device at a sampling rate at least approximating the transit time of a nep-like entity through the sensing volume, and employs pre-sample and post-sample averaging background suppression to recognize a signal amplitude indicative of a nep-like entity. Preferably, the analyzer employs multi-sampling, whereby each signal sample at the sampling rate comprises a plurality of constituent samples.

In accordance with another aspect of the invention, the sensing volume is defined within the outlet section of the nozzle, downstream of the throat.

As another aspect of the invention provides a method for measuring the quantity and size distribution of nep-like entities in a fiber sample. The method includes the steps of individualizing entities in the fiber sample and introducing the entities into a gas flow stream directed into a laterally elongated acceleration/deceleration gas flow nozzle, with a laterally-extending sensing volume defined within the nozzle perpendicular to gas flow through the nozzle, such that multiple individualized entities are simultaneously presented to the sensing volume. The nozzle serves to straighten fiber for presentation to the sensing volume. The method additionally includes a step of sensing the total amount of material within the sensing volume at any given point in time to produce a sensor output signal, and analyzing the sensor output signal to detect and size nep-like entities.

In one form, the step of analyzing comprises sampling the signal at a sampling rate at least approximating the transit time of a nep-like entity through the sensing volume, and employing pre-sample and post-sample averaging background suppression to recognize a signal amplitude indicative of a nep-like entity. Preferably, multi-sampling is employed, whereby each signal sample at the sampling rate comprises a plurality of constituent samples.

In a further embodiment, portions of the fiber samples are processed as a plurality of differing feed rates resulting in a corresponding plurality of signal to background ratios, whereby relatively smaller neps are statistically measured while maintaining a relatively high overall feed rate.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description, taken in conjunction with the drawings, in which:

FIG. 6 is a plot of output waveform of the sensor of FIG. 2, as a function of time; and FIG. 7 is a plot on the same time scale, depicting the result of a multi-sampling technique.

DETAILED DESCRIPTION

Figure 1:
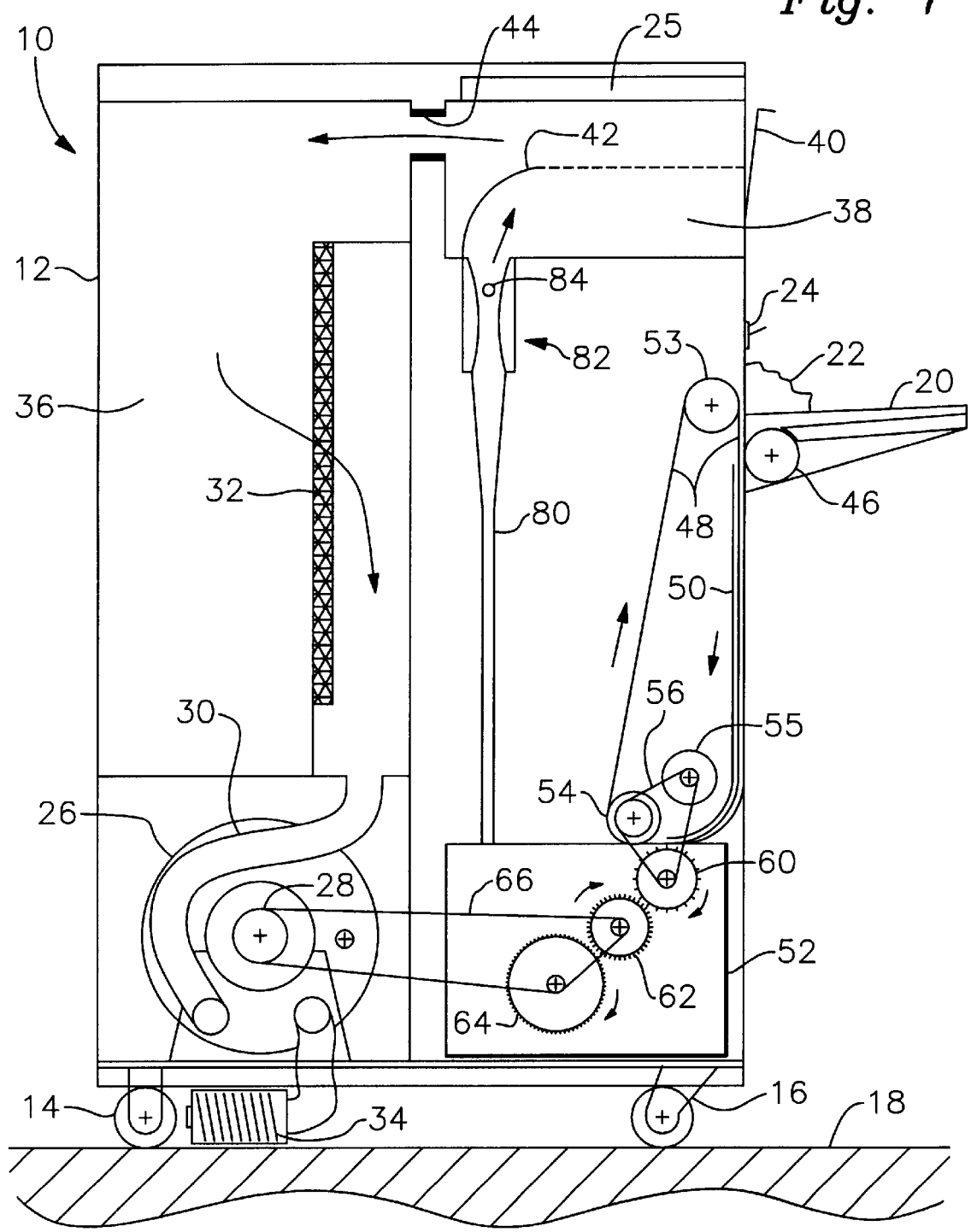
FIG. 1 is a diagrammatic view of a self-contained apparatus for rapidly testing a fiber sample to measure the quantity and size distribution of nep-like entities in the fiber sample.

Referring first to FIG. 1, self-contained apparatus 10 or testing fiber samples has an outer enclosure 12 supported by wheels and casters 14 and 16 for convenient movement about a floor surface 18.

The apparatus includes a feed table, generally designated 20, on which a fiber sample 22 is placed, such as a ten-gram cotton sample. The testing apparatus 10 is activated by means of a on/off switch 24, whereupon the cotton fiber sample 22 is drawn into the machine 10, to be individualized and analyzed. Included within the apparatus is an electronics module 25 comprising an analyzer.

In general, entities comprising the fiber sample 22 are transported through the apparatus 10 by means of a gas flow stream, drawn by a blower unit 26, which accordingly provides suction. The blower 26 is driven by a motor 28 and draws air flow via a blower inlet 30 through a filter 32, and exhausts air via a silencer 34. Following testing, the cotton fiber sample 22, which at that point comprises lint, is collected either in a large lint box 36 or a small lint box 38, and periodically removed. The small lint box 38 has an access door 40, and a removable deflector/screen 42 inside. When the deflector/screen 42 is in place, lint remains in the small lint box 38. When the deflector/screen 42 is removed, lint travels through an opening 44 into the large lint box 36. The small lint box 38 is generally employed for a sample-by-sample mode, and the large lint box 36 for a continuous mode.

The feed table 20, includes a roller 46, and transfers the fiber sample to a feed belt 48 of conventional construction, backed by a stationary plate 50, which delivers the fiber sample to an aeromechanical individualizer 52. The belt 48 is guided by representative pulleys 53 and 54, driven by a motor 55 and drive chain 56.

The aeromechanical individualizer 52 preferably comprises the aeromechanical individualizer disclosed in the above-incorporated concurrently-filed U.S. patent application Ser. No. 08/944,913, filed Oct. 6, 1997, by Frederick M. Shofner and Christopher K. Shofner. However, other individualizers may be employed.

Very briefly, the individualizer 52 includes a cylindrical feed roller 60, a first cylindrical rotating beater wheel 62, and a second cylindrical rotating beater wheel 64. It will be appreciated that the individualizer 52 in FIG. 1 is shown in a highly schematic representation, as a number of elements, such as enclosures for the cylindrical wheels 60, 62 and 64, are omitted. The feed roller 60 is driven by the motor 55 and belt 56 which drives the belt feed 48. The beater wheels 62 and 64 are powered via a drive belt 66 powered by the blower motor.

A significant difference between the individualizer 52 of FIG. 1 and typical prior art individualizers used for testing purposes is the feed rate. Thus, while the purpose of prior art individualizers for testing purposes is to deliver individualized entities one at a time to a downstream sensor, the individualizer 52 of the invention delivers individualized entities at a rate such that multiple entities, particularly fibers, are delivered to a sensor at one time. Thus, the feed belt 48 and cylindrical wheels 60, 62 and 64 are wider than those of individualizers included in prior art apparatus for fiber testing, such as eight inches in width, compared to one inch or less in width in the prior art.

The output of individualizer 52 is delivered to an air stream drawn through a transport duct 80 to an acceleration/deceleration gas flow nozzle 82, including a sensing volume, generally designated 84. The transport duct 80 is rectangular in cross-section, approximately 0.5 inch in thickness (the dimension visible in the FIG. 1 orientation), and approximately eight inches across, consistent with the width of the rolls 60, 62 and 64, and consistent with the relatively higher feed rate of the testing apparatus of FIG. 7, compared to prior art apparatus.

After passing through the acceleration/deceleration gas flow nozzle 82, the fiber and other entities are collected either in the small lint box 34 or the large lint box 36, depending on whether the deflector/screen 42 is in place, for subsequent removal.

Figure 2:
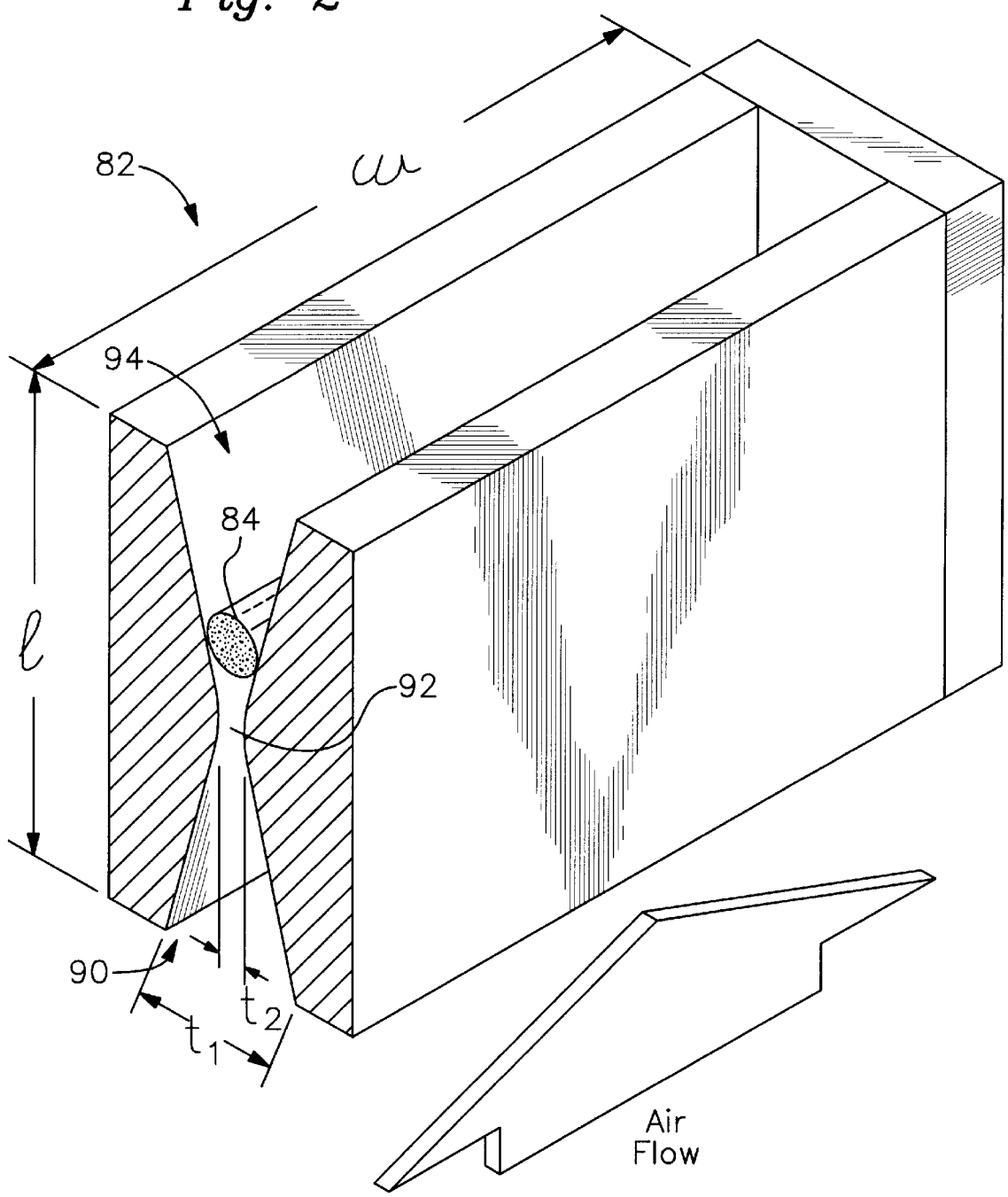
FIG. 2 is enlarged view depicting the acceleration/deceleration gas flow nozzle of the subject invention, including a sensing volume.

With reference now to FIG. 2, the acceleration/deceleration gas flow nozzle 82 includes an inlet section 90 tapering to a minimal cross-sectional area at a throat 92, and an outlet section 94 expanding from the minimal cross-sectional area. It will be appreciated that the underside of the FIG. 2 acceleration/deceleration gas flow nozzle 82 is connected to the transport duct 80 for receiving a flow of individualized entities therefrom, and that acceleration/deceleration gas flow nozzle 82 delivers entities at least initially to the small lint box 34.

In the illustrated embodiment, the acceleration/deceleration gas flow nozzle 82 has a length 1 of six inches. The inlet section 90 has a thickness $t_1$ at its inlet point of approximately 0.5 inches, tapering down to a thickness $t_2$ at the throat 92 of approximately 0.125 inch. The acceleration/deceleration gas flow nozzle 82 is laterally extended, with a width w greater than the throat thickness $t_2$. In the illustrated embodiment, the width w is approximately eight inches. It is this lateral extension which allows multiple fibers to be introduced to the sensing volume 84 at one time.

By way of example, air velocity through the acceleration/deceleration gas flow nozzle 82 is approximately 25 m/sec at the entry point to the inlet section 90 where the thickness is $t_1$ 0.5 inches, and accelerates to 100 m/sec at the throat 92 where the thickness $t_2$ is approximately 0.125 inches.

For purposes of discussion, a nep may be described as a comet-like object comprising a core of a seed coat fragment, tangled fibers or immature fibers, with a tail of attached fibers. A typical nep core diameter is 0.2 mm, and the length of the fiber tail attached may be 25 mm. Typical neps are described in greater detail hereinbelow with reference to FIGS. 4A–4D.

Neps travel through the acceleration/deceleration gas flow nozzle 82 tail first, at least into the sensing volume 84, because the tail comprising fibers is much less dense than the core, and accordingly is subject to greater acceleration. Within the inlet section 90 there is an accelerating flow field, and entities are subject to 1000's of g's acceleration.

Thus, with a throat velocity of 100 m/sec, the velocity of individualized fibers may be 70 m/sec, while the velocity of neps is only 50 m/sec.

Figure 3:
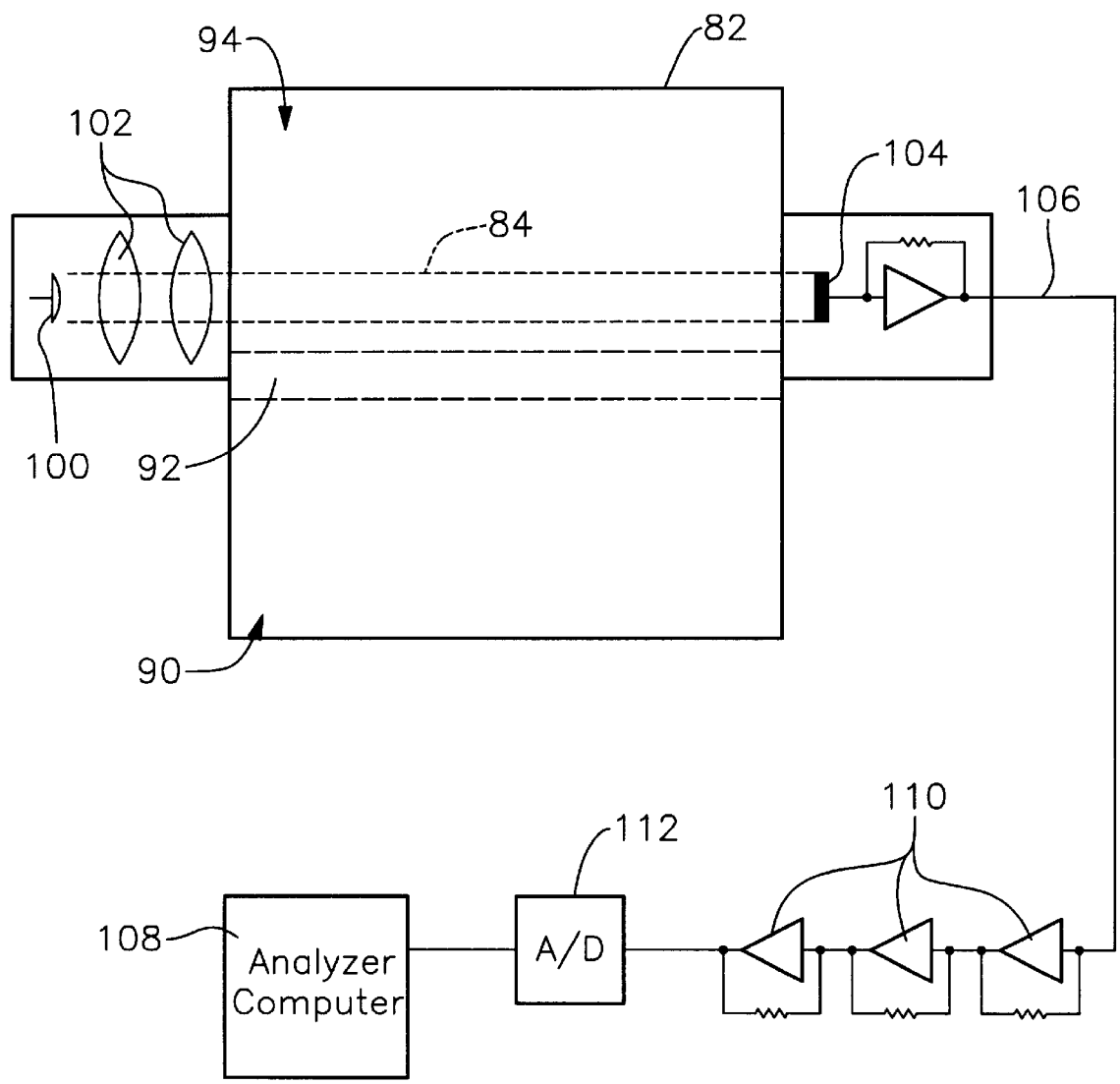
FIG. 3 is a representation of the nozzle of FIG. 2 connected to sensor and an associated electronic analyzer.

With reference to FIG. 3, the sensing volume 84 more particularly is defined by a light source 100, optics 102 and an associated optical sensor 104, producing a signal output 106, connected to an analyzer 108 within the electronics module 25. Appropriate amplifiers 110 condition the signal, which is converted to digital form by an analog-to-digital converter 112.

In the illustrated embodiment, the sensor operates in extinction mode. That is, entities passing through the sensing volume 84 decrease the amount of light received by the detector 104. Thus, signal output increases as the amount of light received by the detector decreases. Neps, being larger, block more light and accordingly produce a greater signal amplitude than fibers.

During typical operation of the subject device, portions of approximately thirty fibers may be present within the sensing volume 84 at any one time, thus producing a randomly fluctuating "background" signal. Since neps are relatively rare compared to fibers, normally only one nep at a time is present within the sensing volume 84.

It will be appreciated that other types of sensors may be employed, so long as a sensing volume is defined. Thus, a light scattering mode sensor alternatively may be employed (including both forward scatter, backward scatter and 90° scatter detectors), employing visible, ultraviolet, or infrared light. As another alternative, a non-optical sensor may be used employing, for example, RF energy or sound.

In typical prior art sensors the sensing volume is positioned coincident with the nozzle throat 92. In the apparatus of FIG. 2, the sensing volume 84 is defined slightly downstream of the throat 92. The main purpose of this sensing volume location 84 is aerodynamic focusing, whereby particles are more nearly centered in the sensing volume 84. Thus, upstream of the throat 92, that is within the inlet section 90, as well as within the throat 92 itself, some entities tend to "hug" the walls. Immediately downstream of the throat 92, at the beginning of the outlet section 94, entities tend to be more nearly centered.

A possible additional benefit of locating the sensing volume downstream of the throat 92 is more uniform velocity of a fiber, by virtue of being within an air flow moving faster than the entity for a greater amount of time. Particularly for a relatively long fiber, which is still undergoing a straightening process, more of the fiber will be up to speed.

Although the sensing volume 84 is downstream of the throat 92, it is important that the sensing volume 84 be located where the gas velocity is still greater than the velocity of the entities.

Figures 4A, 4B:
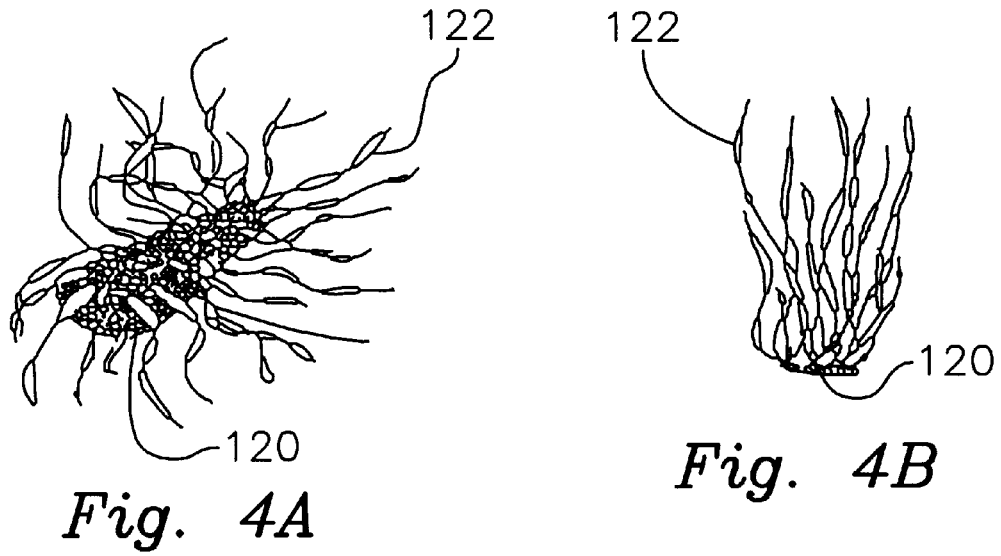
FIGS. 4A, 4B, 4C and 4D depict various nep-like entities.
Figure 4C:
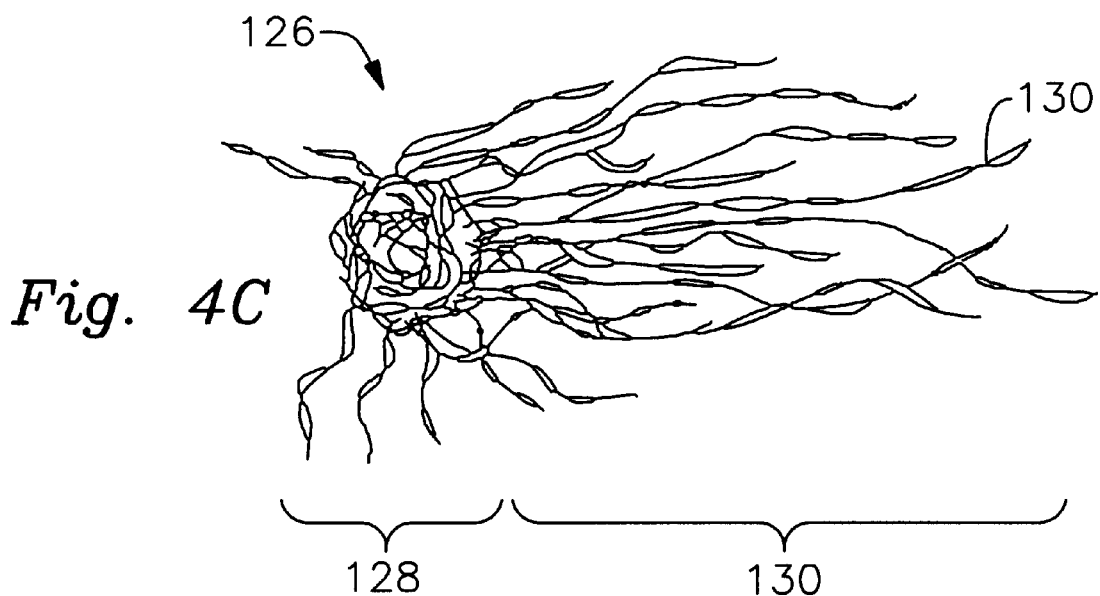
Figure 4D:
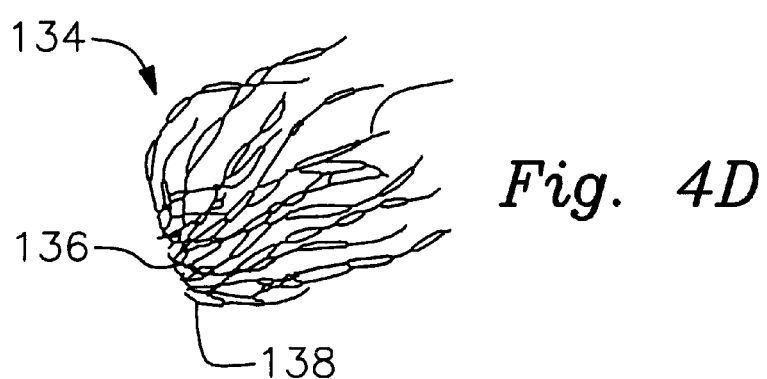

FIGS. 4A, 4B, 4C and 4D depict several forms of textile neps. FIGS. 4A and 4B depict seed coat neps each comprising a fragment of a cotton seed 120 to which cotton fibers 122 are attached. FIG. 4C depicts a mechanically-generated nep 126 which generally comprises a tangled core of fibers 128 along with a less dense tail of trailing fibers 130. FIG. 4D depicts a shiny nep 134 which is generally made of a tightly tangled core 136 of immature fibers, with a less dense tail of trailing fibers 138.

Figure 5:
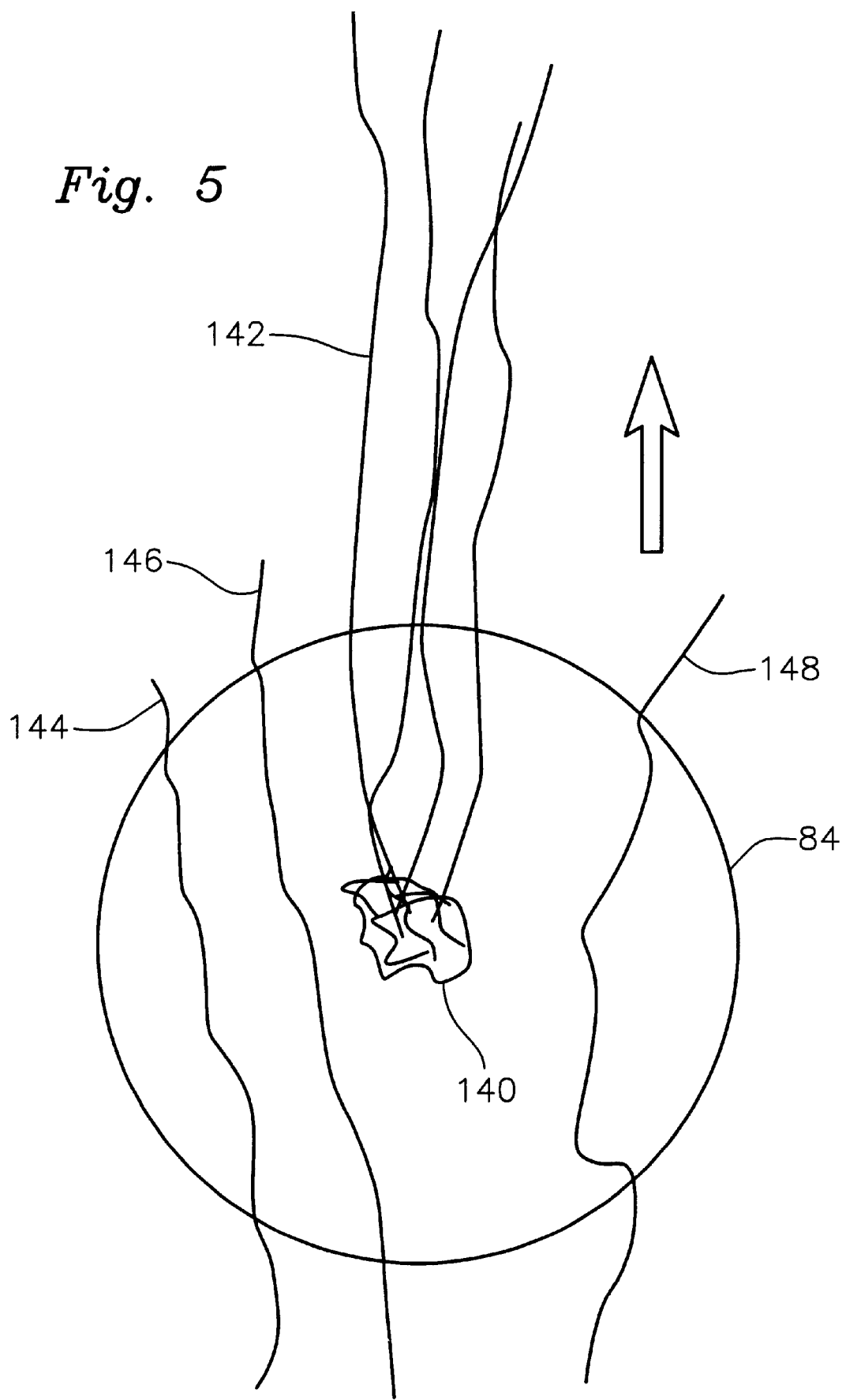
FIG. 5 represents a nep passing through the sensing volume, as well as a plurality of fibers.

FIG. 5 represents a single nep core 140 with a tail 142 passing through the sensing volume 84, together with portions of a plurality of fibers 144, 146 and 148. The sensing volume 84 has a representative diameter of 2.5 mm, while the nep core 140 has a diameter of 0.2 mm. Although portions of only three cotton fibers 144, 146 and 148 are within the sensing volume 84, in addition to the nep 140, portions of many more fibers may be present within the sensing volume 84 at one time, leading to the high throughput of the invention.

FIG. 6 is a plot showing the waveform of the sensor output signal as a function of time, as a nep passes through the sensing volume 84. The extinction mode sensor and associated electronics are designed such that the amplitude of sensor output increases as material enters the sensing volume.

In FIG. 6, the sensor output signal generally designated 150 has a fluctuating background represented at 152 and 154, and a triangularly shaped pulse 156 representing the passage of a nep. The background 152 and 154 is caused by the presence of at least portions of fibers within the sensing volume 84, typically thirty fibers at one time, but the number may vary widely. In a typical fiber sample, there are one thousand times as many fibers as there are neps. Thus, signals such as signal 156 from a nep tend to occur individually whereas background signals such as signals 152 and 154 tend to occur continuously.

Thus, a function of the analyzer 108 is to detect signals resulting from nep entities in a large and fluctuating background of signals resulting from other entities, in particular, fibers.

In the disclosed embodiment, this detection is accomplished by sampling the signal at periodic intervals (that is, at a predetermined and fixed sampling rate) approximating the transit time of a nep-like entity through the sensing volume 84. Then, a technique known as pre-sample and post-sample averaging background suppression is employed to recognize a signal amplitude indicative of a nep-like entity.

Thus, and with reference to FIG. 6, samples are taken at intervals S(i−2), S(i−1), S(i), etc., at, for example, 250-microsecond intervals. One sampling period after each sample is taken, sufficient data is available to determine whether a signal from a nep has been sampled. The sample amplitude is compared to the average amplitude of the sample immediately before (the pre-sample) and the sample immediately after (the post-sample), plus a threshold. If the amplitude is greater, then a nep particle is recognized.

This may be stated in equation form as follows:

$$\text{If } S(i-1) > \frac{S(i-2)+S(i)}{2} + \text{Threshold, then } Nep$$

Preferably, a multi-sampling technique is employed whereby each of the samples S(i−2), S(i−2), S(i), etc. comprises a plurality of constituent samples, as depicted in FIG. 7.

Thus, in FIG. 7, each sample comprises four constituent samples, the amplitudes of which are combined to produce the resultant sample.

It will be appreciated that the sampling technique described hereinabove with reference to FIG. 6 may be characterized as random, in the sense that signals representing nep-like entities can occur at any point in time with reference to the sampling intervals. Thus, in view of the sampling rate at least approximating the transit time of a nep-like entity through the sensing volume, a portion of each nep signal is sensed, but not necessarily the highest amplitude portion of any given nep signal. However, with a sufficiently large sample size, such as a ten gram sample including $2.5 \times 10^3$ neps, statistically a size distribution of nep-like entities can be determined because a statistically sufficient number of nep signals are sampled near their peak amplitude. This allows the generation of a size histogram representing the nep content of the ten-gram sample.

As discussed hereinabove, a feature of the invention is a relatively high throughput, whereby a ten gram sample can be analyzed in about thirty seconds. Such a high throughput is possible with the apparatus of the subject invention, even though many fibers are within the sampling volume at one time, because neps are relatively rare compared to fibers. Nevertheless, the presence of many fibers within the sensing volume at one time in effect increases the background signal, increasing the minimum nep size which can be recognized. At higher throughput rates, signals resulting from relatively smaller neps may be irretrievably buried in the background signal resulting from fibers.

One approach to maintaining a high overall feed rate while maintaining the ability to statistically determine quantities of relatively smaller neps, is to run the apparatus 10 at several feed rates during a sample run to optimize the signal to background ratio for different minimum size neps. Thus, smaller neps can be statistically measured, while maintaining a relatively high overall feed rate.

As another variation, a relatively higher sampling rate can be employed, and digital signal processing (DSP) employed to recognize the various waveforms.

While specific embodiments of the invention have been illustrated and described herein, it is realized that numerous modifications and changes will occur to those skilled in the art. It is therefore to be understood that the appended claims are intended to cover all such modifications and changes that fall within the true spirit and scope of the invention.

What is claimed is:

1. Apparatus for measuring the quantity and size distribution of neps in a fiber sample, said apparatus comprising:

a laterally elongated acceleration/deceleration gas flow nozzle, with a laterally-extending sensing volume defined within said nozzle perpendicular to gas flow through said nozzle, said nozzle serving to straighten fiber for presentation to the sensing volume;

an individualizer for individualizing entities in the fiber sample and introducing the entities into a gas flow stream directed into said nozzle such that multiple individualized entities are simultaneously presented to the sensing volume;

a sensor output device which produces a signal indicating the total amount of material within the sensing volume at any given point in time; and an analyzer connected to said sensor output device for detecting and sizing neps.

2. The apparatus of claim 1, wherein said analyzer samples the signal at a sampling rate at least approximating the transit time of a nep through the sensing volume, and employs pre-sample and post-sample averaging background suppression to recognize a signal amplitude indicative of a nep entity.

3. The apparatus of claim 2, wherein said analyzer employs multi-sampling whereby each signal sample at the sampling rate comprises a plurality of constituent samples.

4. The apparatus of claim 1, wherein said laterally elongated acceleration/deceleration gas flow nozzle includes an inlet section tapering to a minimum cross-sectional area at a throat, and an outlet section expanding from the minimum cross-sectional area, and wherein the sensing volume is defined within said outlet section downstream of said throat.

5. The apparatus of claim 1, wherein the sensing volume is defined by a light beam and an associated optical sensor.

6. A method for measuring the quantity and size distribution of neps in a fiber sample, said method comprising:

individualizing entities in the fiber sample and introducing the entities into a gas flow stream directed into a laterally elongated acceleration/deceleration gas flow nozzle, with a laterally-extending sensing volume defined within the nozzle perpendicular to gas flow through the nozzle, the nozzle serving to straighten fiber for presentation to the sensing volume, such that multiple individualized entities are simultaneously presented to the sensing volume;

sensing the total amount of material within the sensing volume at any given point in time to produce a sensor output signal; and analyzing the sensor output signal to detect and size neps.

7. The method of claim 6, which comprises sampling the signal at a sampling rate at least approximating the transit time of a nep through the sensing volume, and employing pre-sample and post-sample averaging background suppression to recognize a signal amplitude indicative of a nep.

8. The method of claim 7, which comprises employing multi-sampling whereby each signal sample at the sampling rate comprises a plurality of constituent samples.

9. The method of claim 6, which comprises processing portions of the fiber sample at a plurality of differing feed rates resulting in a corresponding plurality of signal to background ratios, whereby relatively smaller neps are statistically measured while maintaining a relatively high overall feed rate.

\* \* \* \* \*